(12) United States Patent
Park et al.

(10) Patent No.: US 6,275,733 B1
(45) Date of Patent: Aug. 14, 2001

(54) DUAL SENSOR RATE RESPONSE PACEMAKER

(75) Inventors: Euljoon Park, Stevenson Ranch; Gene A. Bornzin, Simi Valley; Joseph J. Florio, La Canada, all of CA (US); Saul E. Greenhut, Aurora, CO (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/334,861

(22) Filed: Jun. 16, 1999

(51) Int. Cl.[7] .................................................. A61N 1/365
(52) U.S. Cl. ................................. 607/18; 607/19
(58) Field of Search ........................ 607/9, 17, 18, 607/19, 20, 21, 22, 23, 24, 25, 26

(56) References Cited

U.S. PATENT DOCUMENTS

| | | | |
|---|---|---|---|
| 5,063,927 | 11/1991 | Webb et al. | 128/419 |
| 5,197,467 | 3/1993 | Steinhaus et al. | 128/419 |
| 5,562,711 | 10/1996 | Yerich et al. | 607/17 |
| 5,626,622 | 5/1997 | Cooper | 607/18 |
| 5,722,996 | 3/1998 | Bonnet et al. | 607/17 |
| 5,800,469 | * 9/1998 | Nappholz | 607/18 |

* cited by examiner

Primary Examiner—Jeffrey R. Jastrzab

(57) ABSTRACT

A pacing system which determines a dual indicated rate (DIR) corresponding to a desired pacing rate of the heart of the patient by selecting the maximum between an activity indicated rate (AIR) and a metabolic indicated rate (MIR). The activity indicated rate is a pacing rate that is determined based upon a well-known acceleration-based sensor. The metabolic indicated rate is a desired pacing rate of the heart as determined based upon a well-known metabolic sensor, such as a minute ventilation sensor. Determining the dual indicated rate by selecting between the two rates provided by these two sensors results in the advantageous use of the activity indicated rate during periods of low-level and brisk activity and the use of the metabolic indicated rate during periods of high exertion.

40 Claims, 8 Drawing Sheets

DUAL SENSOR RATE RESPONSE PACEMAKER

FIELD OF THE INVENTION

The present invention relates to implantable cardiac devices such as pacemakers and, in particular, concerns a pacemaker system that provides pacing pulses to the heart to maintain the heart rate at a pacing rate determined based upon signals from an activity sensor and a metabolic demand sensor so as to improve the responsiveness of the pacing rate to the patient's metabolic demand.

BACKGROUND OF THE INVENTION

Since the inception of implantable cardiac devices, these devices have become increasingly sophisticated and more capable over time. The initial implantable cardiac devices were typically comprised of pacemakers which provided electrical pacing pulses to the heart at a generally fixed rate. As the technology has developed, more advanced pacing systems have been implanted in patients which, for example, are capable of providing pacing pulses to the heart only when the pacing system determines that the heart will not provide an intrinsic heart beat. Moreover, these advanced pacemakers are also able to adjust the pacing rate to accommodate different levels of physical activity and corresponding metabolic demand of the patient.

One continuing problem with pacing systems is that the pacing system must preferably be able to adjust the rate at which pacing pulses are delivered to the patient, such that the patient's heart rate more closely tracks the metabolic demand of the patient. In other words, as the patient needs more oxygenated blood to be carried to their extremities during heightened physical activity, the pacing rate of the pacemaker should be increased such that the heart is induced to beat faster to pump more oxygenated blood.

It is generally understood that, with demand-type pacing systems, the desired heart rate is the rate at which the heart must beat to meet the existing metabolic demand of the body. The pacing system typically does not provide pacing pulses at this rate, but simply ensures that either paced events or intrinsic heart events occur at the desired heart rate.

Typically, pacing systems are equipped with sensors which provide signals that are used by the control unit of the pacing system to determine the pacing rate. One such sensor is an activity sensor that typically includes an accelerometer that is positioned within the housing of the control unit that is implanted within the patient's body. As the patient becomes more active, the accelerometer measures the resulting acceleration and provides an activity signal that is indicative of the increased acceleration experienced by the patient. Activity sensors of this type are generally thought to provide a very good indication of the metabolic demand of the patient for newly initiated, brisk, low-level activity. In other words, when the patient initiates a new brisk, low-level activity, such as walking and the like, the accelerometer in the activity sensor provides a good indication of the sudden increase in the level of activity of the patient which generally results in heightened metabolic demand requiring the heart to deliver more oxygenated blood.

While activity sensors of this type are good at providing an indication of the onset of brisk, low-level activity, these sensors do have several shortcomings. For example, the signal that is often provided by such activity sensors becomes blunted when the patient is engaged in high exertion exercise. In other words, when the patient is heavily engaged in a particular physical activity, the activity signal may not provide a sufficient indication to the control unit of the need for more oxygenated blood as a result of the increased activity. For example, the output signal from a typical prior art activity signal is generally inaccurate for assessing the patient's actual metabolic need when the patient is performing an action like carrying a heavy object. The degree of acceleration detected by the activity sensor is likely to correspond to a perceived low metabolic demand activity, such as walking, and would not account for the increase in metabolic demand as a result of carrying the heavy object. Moreover, acceleration-based activity sensors are also subject to providing false readings as a result of the patient experiencing accelerations that are unrelated to physical activity, such as, for example, the patient travelling on a bumpy road in a vehicle.

Another type of sensor that is used to provide an indication of metabolic demand is referred to as a metabolic rate sensor. One common type of metabolic rate sensor is a minute ventilation sensor which measures the respiration rate and tidal volume of the patient's respiration. It is believe that the rate at which the patient is breathing and the volume of air being breathed is indicative of the metabolic demand of the patient. One typical way of obtaining a minute ventilation signal is to periodically measure the transthoracic impedance between a lead implanted within the patient's heart and an indifferent electrode, such as the housing of the implanted pacemaker control unit. As the transthoracic impedance is proportional to the chest volume, measuring this particular impedance value provides an indication as to the degree to which the patient's chest is expanding and contracting and the rate at which such expansion and contraction is occurring. The greater the patient's breathing rate and the greater the tidal volume of the breaths, the more likely it is that the patient has a heightened need for delivery of oxygenated blood by the heart.

While metabolic rate sensors, such as minute ventilation sensors, provide a strong indication of the metabolic demand of the patient, these sensors also have several disadvantages for use in determining the pacing rate and desired heart rate. In particular, the values provided by these sensors often lag in time behind the actual metabolic demand of the patient. Consequently, these sensors are typically not particularly well suited for providing the sole indication of the actual metabolic demand of the patient when the patient is initiating or ceasing physical exertion.

To address the problems associated with both of these types of sensors, rate responsive pacing systems have been developed which utilize the signals from several different types of sensors to determine a desired pacing and heart rate. For example, U.S. Pat. No. 5,626,622 combines the signals from an activity sensor and a minute ventilation sensor such that when the physical activity undergoes a transition, the combined response is predominantly derived by the physical activity sensor. Hence, the pacing rate corresponds to a pacing rate that is expected to satisfy the metabolic need for the observed level of activity as indicated by the activity sensor. During rest and steady state periods and rest or sustained exercise periods, the combined response of both the sensors, which determines the pacing rate, is predominantly derived from the minute ventilation sensor. Similarly, U.S. Pat. No. 5,562,711 is structured in such a manner that the activity sensor has an influence at lower pacing rates, such as when the patient is at rest. Various weighting factors are used so that when the patient is not at rest, a minute ventilation sensor provides the signal which is used to determine the desired heart rate and pacing rate. With both of the algorithms disclosed in these patents, the determination of the desired heart rate often involves comparatively complex algorithms which are expensive to implement and difficult to evaluate for diagnostic purposes. Further, these algorithms often fail to provide an optimum indication of a desired heart rate during recovery from physical exercise. Moreover, these algorithms are generally not capable of providing a desired heart rate suitable for a sleeping or rest mode of the patient.

Hence, there is a need for a pacing system and method which is capable of determining a desired heart rate based upon the inputs from an activity sensor and a metabolic rate sensor, such as a minute ventilation sensor. To this end, there is a need for a pacing system which is capable of simply and effectively determining the desired heart rate based upon the inputs from an activity sensor and a metabolic rate sensor such that the desired rate is clearly determined from the inputs of the two sensors for diagnostic purposes and also such that the desired rate has better response during periods of recovery from exercise of the patient.

SUMMARY OF THE INVENTION

The aforementioned needs are satisfied by the pacing system of the present invention which is comprised of an activity sensor means for providing an activity indicated rate, a metabolic sensor means for providing a metabolic indicated rate, and a control means which receives the activity indicated rate and the metabolic indicated rate signal and produces a dual indicated rate which is used to determine the rate at which the control means will induce the delivery of pacing pulses to the heart of the patient. In this way, the heart will beat at a desired rate corresponding to the metabolic needs of the patient.

The control means preferably selects the dual indicated rate as being the maximum of the activity indicated rate and the metabolic indicated rate while the patient is in a non-resting mode. By selecting the maximum of the activity indicated rate and the metabolic indicated rate as the dual indicated rate, the control means will induce delivery of pacing pulses to the heart of the patient such that the heart will beat at a rate which is most responsive to the activity indicated rate at lower levels of patient exercise and will induce the delivery of pacing pulses to the heart such that the heart will beat at a desired rate that corresponds to the metabolic indicated rate at higher levels of patient exercise.

In one aspect of the invention, the control means induces the delivery of pacing pulses to the patient such that the patient's heart rate corresponds to the activity indicated rate provided that the activity indicated rate is less than a preselected maximum value. In one embodiment, the preselected maximum is a maximum sensor rate value selected by the implanting or treating physician. In another embodiment, the maximum activity indicated rate is defined by the formula 0.7×(220−the age of the patient)−10 ppm.

In another aspect of the invention, a method of determining a dual indicated rate is provided. The method comprises the steps of obtaining an activity indicated rate, obtaining a metabolic indicated rate, determining the maximum between activity indicated rate and the metabolic indicated rate, and setting the dual indicated rate as being equal to the maximum of the activity indicated rate or the metabolic indicated rate.

It will be appreciated that the pacing system and method of the present invention provides a simple straight-forward algorithm for determining between an activity indicated rate and a metabolic indicated rate as the dual indicated rate for the patient given the detected activity level and metabolic rate. Since the activity indicated rate is typically more responsive to changes in the patient's metabolic need at lower levels of activity, the system and method of the present invention provide a quickly responsive rate at these lower levels of physical activity of the patient. Similarly, since the metabolic indicated rate is more responsive to the metabolic demands of the patient at higher levels of patient activity, selecting the dual indicated rate as corresponding to the metabolic indicated rate at higher levels of patient activity and exertion results in a heart rate that more closely tracks the actual metabolic and physiological needs of the patient.

Hence, the algorithm allows for easier determination of which rate is being used to provide the pacing rate for diagnostic purposes. Moreover, the algorithm is simpler to implement as it does not require additional components and the processing required to determine the dual indicated rate is less which conserves limited battery power in the implanted pacing system. These and other objects and advantages of the present invention will become more apparent from the following description taken in conjunction with the accompanying drawings.

DETAILED DESCRIPTION OF THE PREFERRED EMBODIMENT

Reference will now be made to the drawings wherein like numerals refer to like parts throughout.

Figure 1A:
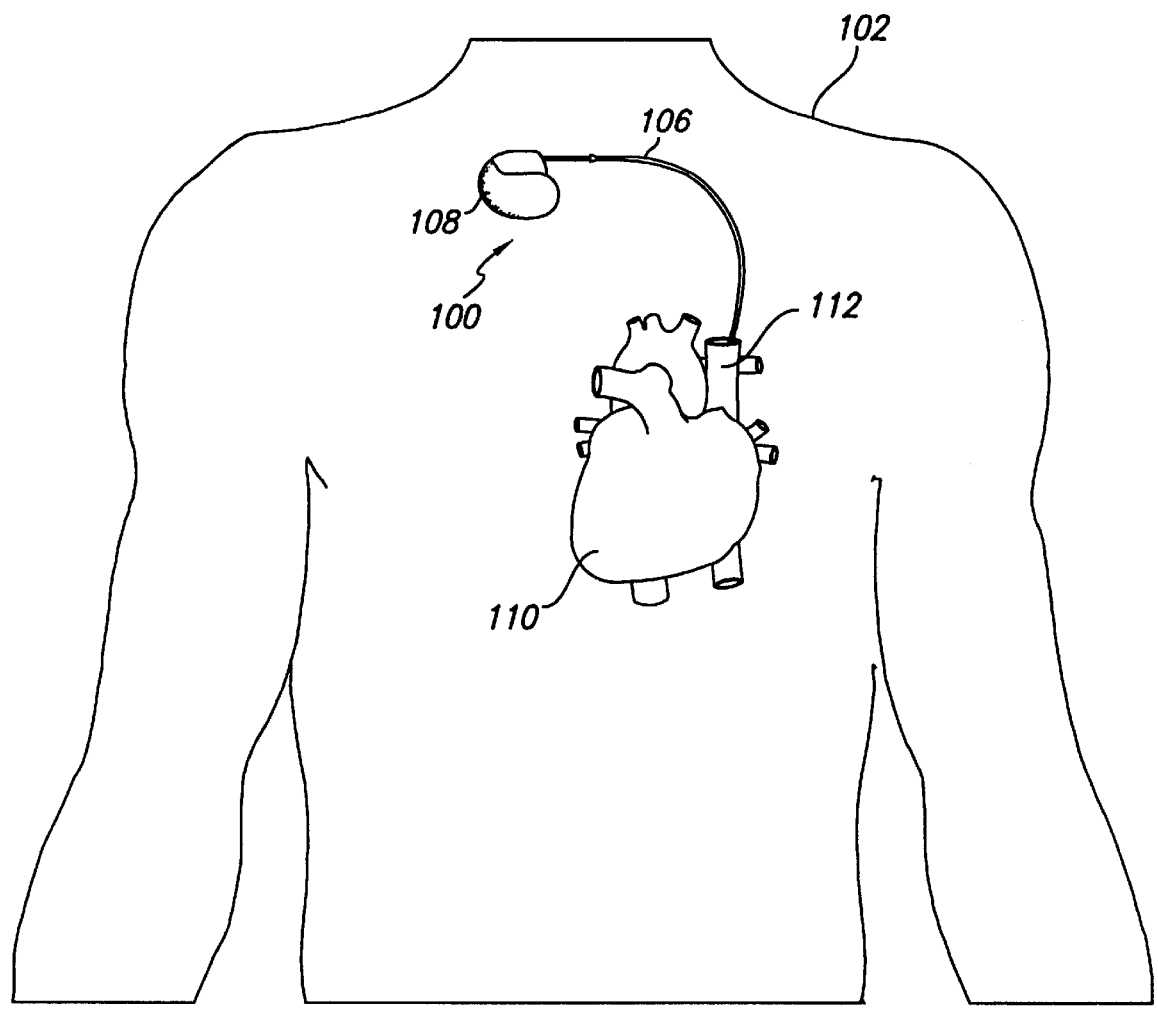
FIG. 1A is an illustration of an exemplary pacing system implanted in a patient.

Referring to FIG. 1A, there is shown an illustration of generally where an implantable cardiac device 100, such as a pacing system, in accordance with one embodiment of the present invention, may be implanted in a patient 102. In accordance with the conventional practice in the art, a control unit 104 (FIG. 1B), is housed within a hermetically sealed, biologically inert outer canister or casing 108, which may itself be conductive and thus serve as an indifferent electrode in the pacing system's pacing/sensing circuit, as will be described in greater detail below. One or more pacing leads, collectively identified as 106, are electrically coupled to the control unit 104 in the casing 108 in a conventional manner and are implanted so as to extend into the heart 110 of the patient via a vein 112. Disposed generally near the distal end of the leads 106 are one or more exposed conductive electrodes for receiving electrical cardiac signals and for delivering electrical pacing pulses to the heart 110. As will be appreciated by those of ordinary skill in the art, the leads 106 may be implanted with their distal ends situated in either the atrium or the ventricle of the heart 110 or both.

Figure 1B:
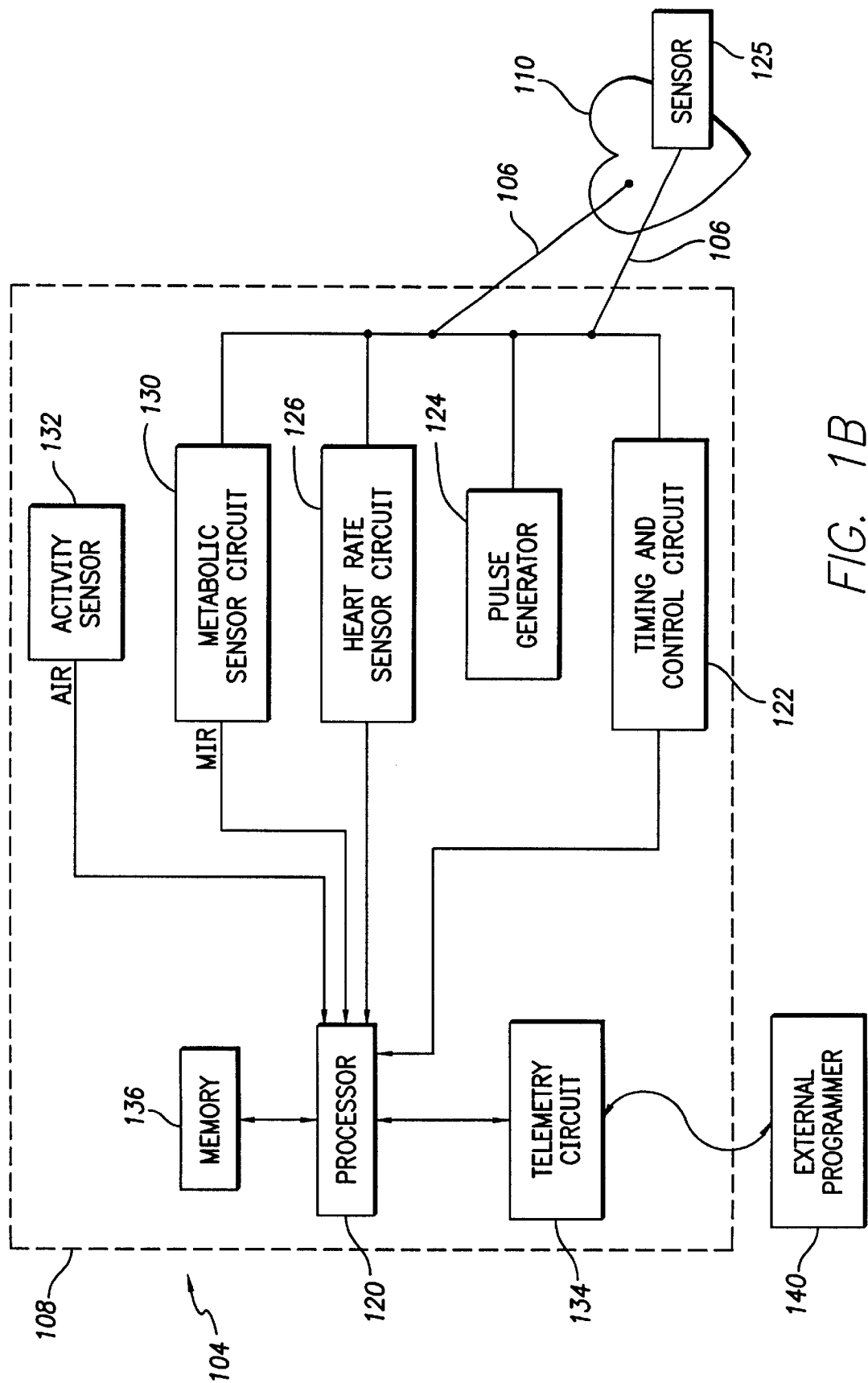
FIG. 1B is a block diagram of one embodiment of an implantable pacing system according to the present invention.

FIG. 1B is a functional block diagram illustrating one embodiment of a typical implantable cardiac device 100. In this embodiment, the implantable cardiac device 100 is a pacing system which incorporates a control unit generally designated 104 which is generally positioned within the casing 108 as described above, and a plurality of leads 106 that are configured to be positioned within the chamber of the patient's heart 110. The control unit 104 includes a processor 120 which provides output signals to a timing and control circuit 122. Upon receipt of the output signals from the processor 120, the timing and control circuit 122 induces a pulse generator 124 to produce therapeutical electrical stimulation that is to be transported via the leads 106 to stimulate the heart 110. In this embodiment, the processor 120 induces the timing and control circuit 122 to cause the pulse generator 124 to provide pacing pulses of a typical configuration in a well-known fashion to the heart at a rate that is to be determined in accordance with the principles of the present invention, as will be described in greater detail below.

Further, the processor 120 receives input signals from a heart rate sensor 125 via a heart rate sensor circuit 126. In one embodiment, the sensor 125 is actually comprised of an implanted lead 106 that is positioned within one of the chambers of the heart 110 so as to provide an intracardiac electrogram (IEG) signal to the processor 120 in a well-known manner. Hence, the processor 120 is configured to receive a signal which is indicative of the activity of the heart 110 and is further configured to provide therapeutic electrical stimulation to the heart based, at least in part, upon the IEG signal.

In this embodiment, the processor 120 also receives a metabolic indicated rate signal from a metabolic sensor circuit 130. In the preferred embodiment, the metabolic sensor circuit 130 is comprised of a minute ventilation sensor circuit which is adapted to periodically measure the transthoracic impedance of the patient. In one embodiment, the metabolic sensor circuit 130 induces the delivery of transthoracic measurement pulses from the leads 106 implanted within the heart and then measures the return on an indifferent electrode such as the casing 108. The transthoracic measurement pulses provide a resulting measurement that can be filtered so as to remove heart fluctuation components and the like in a well known manner so that signals indicative of the transthoracic impedance can be obtained.

As is well understood in the art, transthoracic impedance is shown to be proportional to a minute ventilation parameter of the patient. As noted above, the minute ventilation parameter is a product of both the respiration tidal volume and rate and is a very good physiological indicator of the change in the metabolic demand of the patient. In particular, it has been observed that the greater the rate at which the patient breaths and the deeper the breaths, i.e., the greater the tidal volume, the greater the metabolic demand of the patient. When the patient is breathing faster and deeper, it is generally because the patient is engaged in a more strenuous physical activity requiring greater delivery of oxygenated blood by the heart. Hence, minute ventilation can provide a parameter from which a metabolic indicated rate can be determined.

In one example, transthoracic impedance and, thus, the minute ventilation parameter is sampled over a discrete period of time and the measured value over the period of time is translated into a metabolic indicated rate using known algorithms. The algorithms provide a desired heart rate that is believed to be necessary to meet the metabolic demands corresponding to a particular measured minute ventilation parameter.

As a consequence, the metabolic sensor circuit 130 can be used to develop a minute ventilation or metabolic indicated rate (MIR) in a well-known manner. In particular, the metabolic sensor circuit 130 can develop a metabolic indicated rate, such as a minute ventilation indicated rate, in a manner similar to the manner disclosed in U.S. Pat. No. 5,626,622.

Similarly, the processor 120 also receives signals from an activity sensor 132. In one embodiment, the activity sensor 132 is comprised of an acceleration-based activity sensor, such as the acceleration-type sensor disclosed in U.S. Pat. No. 5,626,622 which is hereby incorporated by reference in its entirety. The activity sensor 132 provides a signal known as the activity indicated rate (AIR).

In one exemplary embodiment, the activity sensor 132 is comprised of a piezoelectric sensor that creates an electrical signal in response to accelerations of the patient's body. If the acceleration signals are greater than a threshold amount, the signal is digitized and a counter is incremented. The activity sensor 132 then provides a count value at periodic intervals. The magnitude of the count value over a selected period of time is representative of the activity of the patient. This value can then be translated into an activity indicated rate (AIR) using known techniques which comprises a desired heart or pacing rate needed to meet the perceived metabolic needs of a patient experiencing the detected degree of activity. It will be appreciated from the following discussion that any of a number of different ways of determining the activity level of the patient and developing a corresponding activity indicated rate (AIR) known in the art can be used without departing from the spirit of the present invention.

The metabolic indicated rate (MIR) and the activity indicated rate (AIR) are preferably determined values which are the rate at which the activity sensor 132 and the metabolic sensor circuit 130 indicate should be the heart rate to meet the perceived metabolic needs of the patient. It will be appreciated that the exact manner in which the activity indicated rate or the metabolic indicated rate can be calculated can be done in any of a number of well-known fashions without departing from the spirit of the present invention.

The system and the method of the present invention provide a system for determining a dual indicated rate (DIR), based upon the activity indicated rate (AIR) and the metabolic indicated rate (MIR).

The dual indicated rate (DIR) corresponds to the actual heart rate of the patient that is determined to satisfy the detected metabolic needs of the patient based upon the activity indicated rate (AIR) and the metabolic indicated rate (MIR). This rate is then used by the processor 120 of the control unit 104, in a well-known manner, to increase the pacing rate of the heart such that the resulting heart rate corresponds to the dual indicated rate (DIR).

As will be described in greater detail below, the dual indicated rate (DIR), in this embodiment, corresponds to the larger between the activity indicated rate (AIR) and the metabolic indicated rate (MIR) during each measurement period. In one embodiment, the contribution of the activity indicated rate (AIR) is capped at a maximum value such that if the metabolic indicated rate (MIR) exceeds the maximum value of the activity indicated rate (AIR) then the dual indicated rate (DIR) will correspond to the metabolic indicated rate (MIR).

Figure 2:
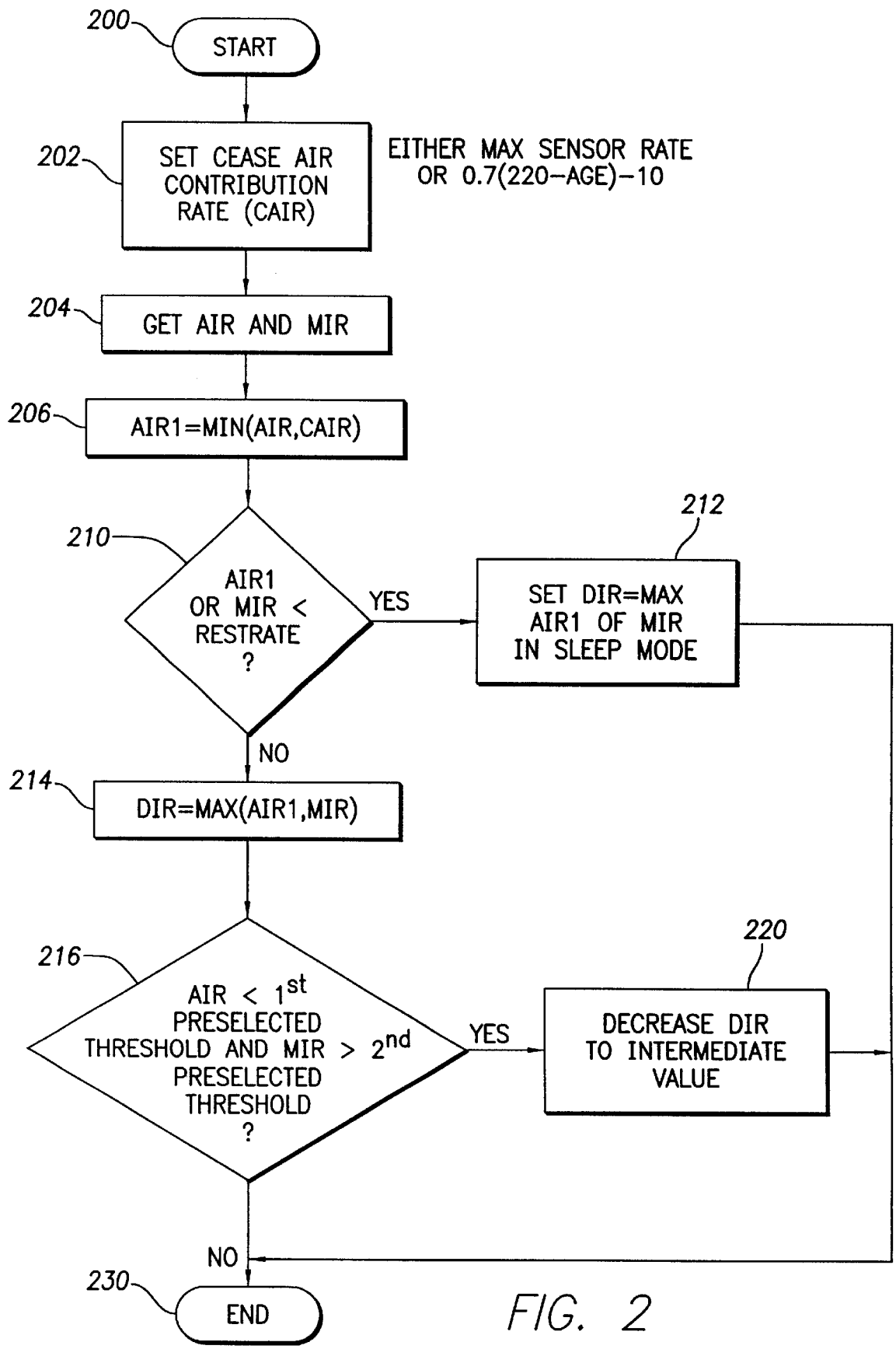
FIG. 2 is a flow chart of an algorithm for determining a dual indicated rate of the pacing system of FIG. 1A and 1B.

Referring specifically to the flow chart of FIG. 2, the algorithm by which the dual indicated rate (DIR) is determined is illustrated. In particular, the processor 120, from a start state 200, initially proceeds to a state 202 wherein the maximum activity indicated rate (CAIR) of the algorithm will be set. As described above, in the preferred embodiment of the algorithm, a maximum value of the activity indicated rate is set by the treating physician such that an activity indicated rate which exceeds the maximum activity indicated rate (CAIR) will be ignored. In one embodiment, the maximum activity indicated rate (CAIR) is set to be equal to the value as defined by formula 1 below:

$$CAIR = 0.7(220 - Age) - 10 \text{ ppm} \quad (1)$$

wherein the Age is equal to the age of the patient. As will be described in greater detail below, when the actual activity indicated rate determined based on the signals from the activity sensor 132 exceeds the maximum activity indicated rate (CAIR), then the processor 120 will set the dual indicated rate (DIR) as equal to either the maximum activity indicated rate (CAIR) or the metabolic indicated rate (MIR) when the metabolic indicated rate exceeds the maximum activity indicated rate (CAIR).

Once the maximum activity indicated rate (CAIR) is set, in state 202, the processor 120 then proceeds to obtain the activity indicated rate (AIR) and the metabolic indicated rate (MIR) from the activity sensor 132 and the metabolic sensor circuit 130 (FIG. 1B). The AIR value and the MIR value are periodically updated by the activity sensor 132 and the metabolic sensor circuit 130 as described above. Hence, the processor 120 periodically obtains a new AIR value and a MIR value from which to determine a DIR value in the manner that will be described in greater detail below.

The processor 120 then, in a state 206, sets an interim activity indicated rate value (AIR1) as being equal to the minimum of the activity indicated rate (AIR) as provided by the activity sensor 130 in state 204 or the maximum activity indicated rate (CAIR) as set in state 202. By setting this interim activity indicated rate value (AIR1) as the minimum between the AIR value and the CAIR value, the processor 120 ensures that any contribution to the ultimately determined dual indicated rate (DIR) resulting from the activity indicated rate signal provided by the activity sensor 132 is limited to the maximum value CAIR as set in state 202.

The processor 120 then determines in decision state 210 whether the interim activity indicated rate (AIR1) or the metabolic indicated rate (MIR) is less than or equal to a predetermined rest or sleep rate value. As is understood in the art, the activity indicated rate (AIR) or the metabolic indicated rate (MIR) may be indicative of the person being at rest or asleep. In this condition, the activity signal of the patient and a metabolic signal, such as minute ventilation, will be of a relatively low value indicating a low metabolic need of the patient. As such, it is typically desirable to lower the desired heart rate and, thus, the pacing rate, to a preselected rest rate so as to not disturb the resting of the patient and so as to conserve limited battery power.

If it is determined state 210 that either the interim activity indicated rate (AIR1) or the metabolic indicated rate (MIR) is less than the rest rate, then the dual indicated rate (DIR) will be set, in state 212, as equal to a sleep mode value of the activity indicated rate or the metabolic indicated rate. In particular, it will be appreciated that some activity sensors and some metabolic sensors will have a sleep mode. If only one of the activity sensors 132 or the metabolic sensors 130 has such a sleep or rest mode, then the dual indicated rate (DIR) will be set to either the measured interim AIR1 value or the MIR value, respectively. If both the activity sensor 132 and the metabolic sensor 130 have a sleep or rest mode setting, then the dual indicated rate (DIR) for this time period will be set, in state 212, as equal to the largest of either the measured CAIR value or the MIR value. Alternatively, if the activity sensor 132 or the metabolic sensor circuit 130 indicate that the patient is in a sleep mode or rest mode, the DIR may be set to a pre-selected sleep mode rate. In this way, the dual indicated rate (DIR) will be equal to a lowered sleep or rest mode value.

If neither the interim activity indicated rate (AIR1) or the metabolic indicated rate (MIR) is less than the rest rate, then the dual indicated rate (DIR) will be set, in state 214, as equal to the maximum of the interim activity indicated rate (AIR1) or the metabolic indicated rate (MIR). As the interim activity indicated rate (AIR1) is capped at a maximum activity indicated rate (CAIR), such as the rate as defined by Formula (1) above, the dual indicated rate (DIR) will be the larger of the interim activity indicated rate (AIR1) or the metabolic indicated rate. This is true unless the interim activity indicated rate (AIR1) exceeds the maximum activity indicated rate (CAIR) set in state 202 and the metabolic indicated rate (MIR) is less than the maximum value (CAIR), then the desired indicated rate (DIR) is equal to the maximum activity indicated rate (CAIR) as set in state 202. If, however, the metabolic indicated rate (MIR) is greater than the activity indicated rate (CAIR), the metabolic indicated rate (MIR) defines the dual indicated rate (DIR).

As was discussed above, the activity indicated rate (AIR) is preferably calculated using an acceleration based sensor. Hence, during periods of relatively low physical activity on the part of the patient or onset of physical activity, the activity indicated rate (AIR) is typically higher than the metabolic indicated rate (MIR) due to the lag between the metabolic indicated rate (MIR), as determined using a minute ventilation calculation as described above, and the actual metabolic need of the patient. Hence, during periods of relatively low physical activity and the onset of exertion of the patient, the activity indicated rate (AIR) will typically define the desired indicated rate of the pacing system 100.

During periods of relatively greater physical activity and exertion by the patient, the metabolic indicated rate (MIR) will generally increase as a result of deeper and more rapid breathing by the patient. Preferably, both the activity indicated rate (AIR) values and the metabolic indicated rate (MIR) values used in this embodiment are scaled so that these values have a general correspondence to each other using well known scaling techniques, such as the techniques described in U.S. Pat. No. 5,626,622. For example, the minimum and maximum measured AIR and MIR values may be equated so as to scale the values to each other.

Hence, during periods of greater physical exertion, the metabolic indicated rate (MIR), which is related to the minute ventilation determination obtained by the minute ventilation sensor circuit 130, will determine the dual indicated rate (DIR). Hence, in the exertion range, where the metabolic indicated rate (MIR) is above the maximum activity indicated rate (CAIR), the dual indicated rate (DIR) will be set as equal to the metabolic indicated rate (MIR) which is believed to be more proportional to the actual metabolic workload of the patient as the activity indicated rate (AIR) is typically known to be blunted during periods of high exertion exercise. As will be described in greater detail below, during recovery, the dual indicated rate (DIR) will usually be selected as being equal to the metabolic indicated rate (MIR) as this is typically higher than the AIR value due to the lag between MIR and actual metabolic need.

As illustrated in FIG. 2, the processor 120 will periodically institute a cross-check algorithm in decision state 216. In particular, the processor 120 will periodically determine in decision state 216 whether the metabolic indicated rate (MIR) indicates a high level of metabolic need with the activity indicated rate (AIR) simultaneously indicating a low metabolic need. When there is a large discrepancy between the metabolic indicated rate (MIR) and the activity indicated rate (AIR) an abnormal condition is to be assumed and the dual indicated rate (DIR) will not be allowed to rise as high as the metabolic indicated rate (MIR). Specifically, if the MIR is above a preselected threshold near the maximum value for the MIR and the AIR is below a preselected threshold near the minimum value for the AIR, the processor 120 will, in state 220, decrease the dual indicated rate (DIR) to a preselected rate intermediate value using an algorithm such as the algorithm disclosed in U.S. Pat. No. 5,626,622. In particular, in one embodiment, the difference between the MIR and the AIR is determined and the DIR is set to some value that is between these two values. In this way, the DIR is not allowed to rise as high as the MIR and can be slowly decreased during recovery periods. In particular, this cross-checking algorithm is particularly effective during recovery periods where at the cessation of strenuous physical activity the MIR tends to lag actual metabolic need, but the AIR quickly is demonstrating the cessation of the physical activity. In such a situation, the DIR is allowed to be gradually reduced thereby more closely approximating the actual physiological needs of the patient.

The processor 120 repeats the process defined by states 220 to 230 during normal operation of the pacing system 100. In this way, a dual indicated rate can be determined and used as a basis for defining a desired heart rate and pacing rate. The DIR can then be used to determine a pacing rate at which the timing and control circuit 122 will induce the pulse generator 124 to deliver pacing pulses to the heart 110 in the absence of intrinsic heart events. Naturally, the pacing rate will not actually necessarily result in the pulse generator 124 generating a pacing pulse during each cycle as the pacemaker system 100 may be a demand-type pacemaker. Rather, the dual indicated rate provides a value which the processor 120 can use to calculate the time intervals during which either an intrinsic cardiac event or a pacing pulse should be delivered to the heart 110 in order for the heart to meet the metabolic needs of the patient.

By using an algorithm, such as the algorithm described above, the activity indicated rate (AIR) predominates during lower levels of activity where the activity indicated rate (AIR) is more indicative of the actual metabolic need of the patient. Similarly, during periods of high exertion exercise, the metabolic indicated rate (MIR) will be used as it is more proportional to the metabolic need of the patient.

Figure 3:
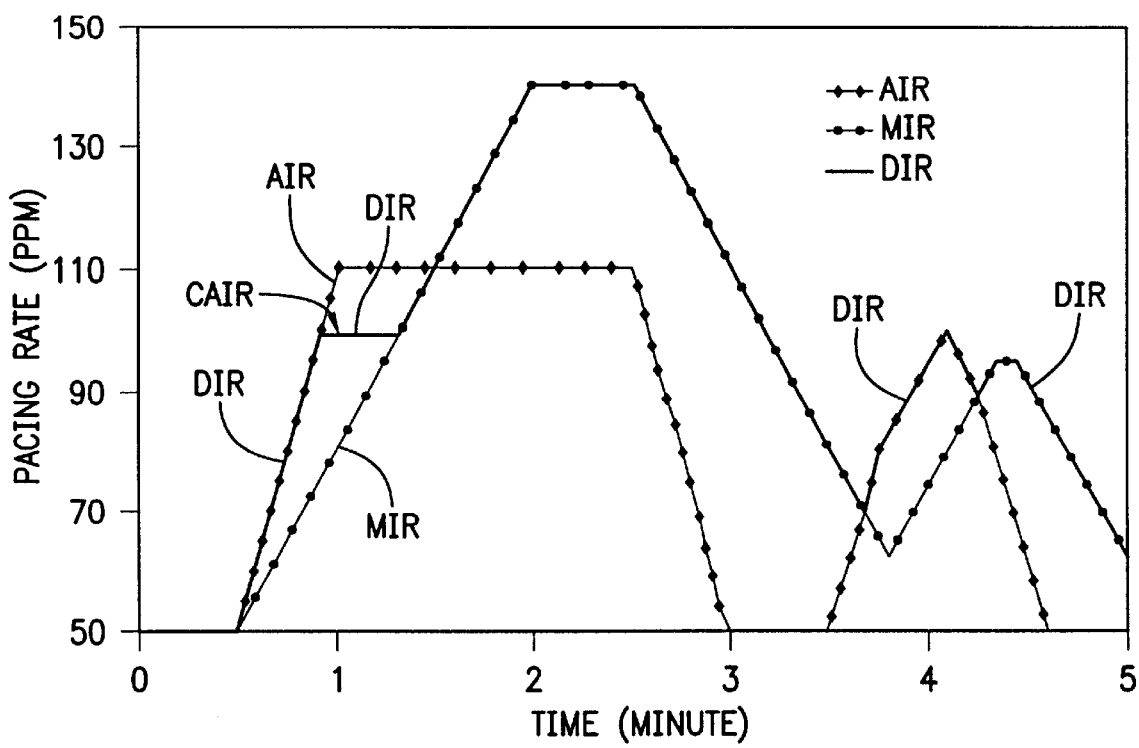
FIG. 3 is a schematic illustration illustrating the performance of the pacing system as it determines the dual indicated rate in accordance with the algorithm of FIG. 2.

FIG. 3 is a diagram which illustrates how the algorithm described in connection with FIG. 2 would determine a dual indicated rate (DIR). In particular, it will be appreciated that the activity indicated rate (AIR) responds more quickly to metabolic needs than the metabolic indicated rate (MIR) as is evidenced by the MIR waveform lagging the AIR waveform. Hence, during the initial low-level activity, it is desirable to use the AIR waveform as the desired indicated rate to provide more immediate response to the patient's metabolic need. As is further indicated in the diagram of FIG. 3, the activity indicated rate (AIR) caps at a maximum value (CAIR) which, in this embodiment, is approximately 110 ppm as defined by Formula (1). Generally, the capping of the activity indicated rate (AIR) can be viewed as the result of the detected acceleration resulting from greater activity of the patient increasing dramatically to essentially a maximum value and then remaining constant at that maximum value. However, sustained activity by the patient will result in even greater metabolic need than as indicated by the metabolic indicated rate. Consequently, the dual indicated rate (DIR) will then track the metabolic indicated rate (MIR) when the metabolic indicated rate (MIR) exceeds the maximum activity indicated rate (CAIR) as indicated in FIG. 3.

During the recovery period, the dual indicated rate (DIR) will typically follow the metabolic indicated rate (MIR) even though the metabolic indicated rate (MIR) lags the activity indicated rate (AIR) as the MIR typically has a higher value. Subsequently, the dual indicated rate (DIR) will follow whichever of the activity indicated rate (AIR) or metabolic indicated rate (MIR) that is higher. Hence, in post-recovery activity, the dual indicated rate (DIR) can quickly respond to a change in the activity indicated rate (AIR) rather than having to follow the slower responding metabolic indicated rate (MIR).

Figure 4A:
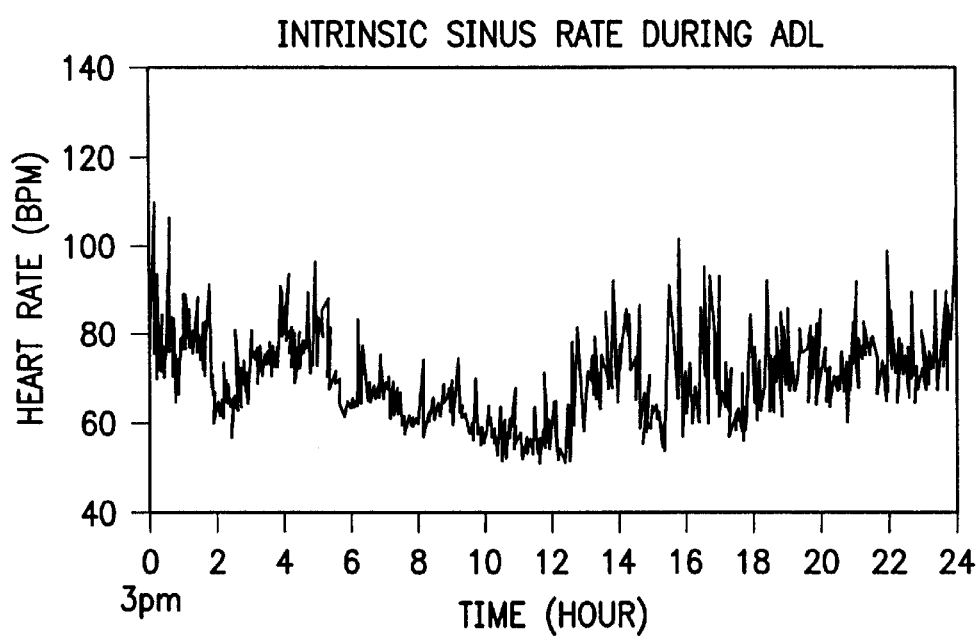
FIGS. 4A–4D are graphical representations of 24 hours worth of cardiac data obtained from a patient wearing a Holter monitor with corresponding activity indicated rate, minute ventilation indicated rate, and a desired dual indicated rate as determined according to the algorithm of FIG. 2 while the patient undergoes 24 hours of average daily living.
Figure 4B:
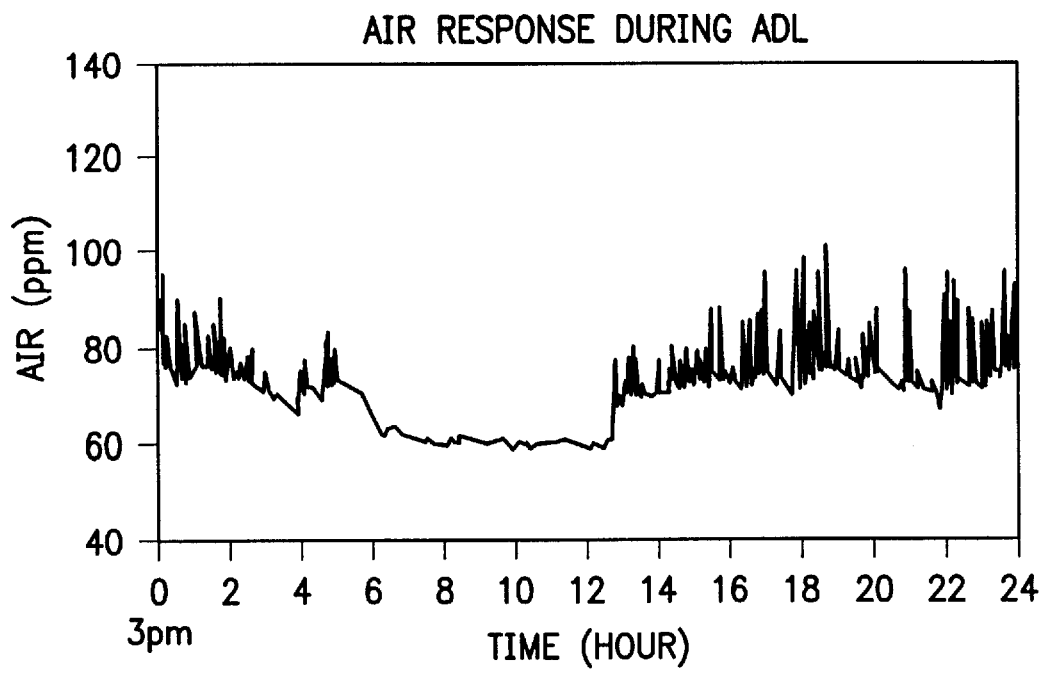
Figure 4C:
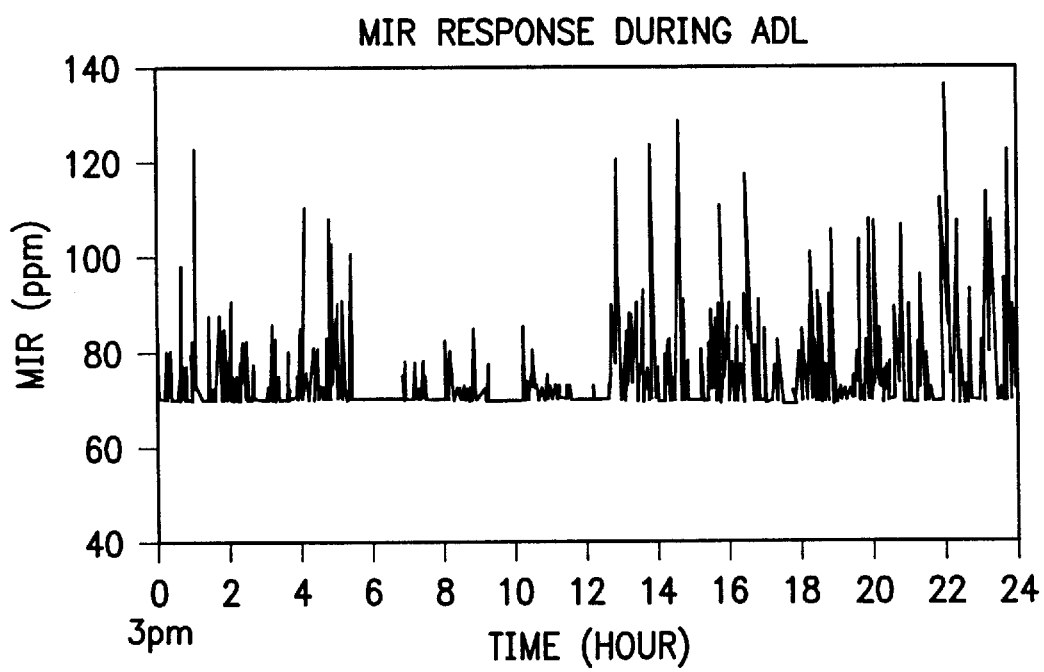
Figure 4D:
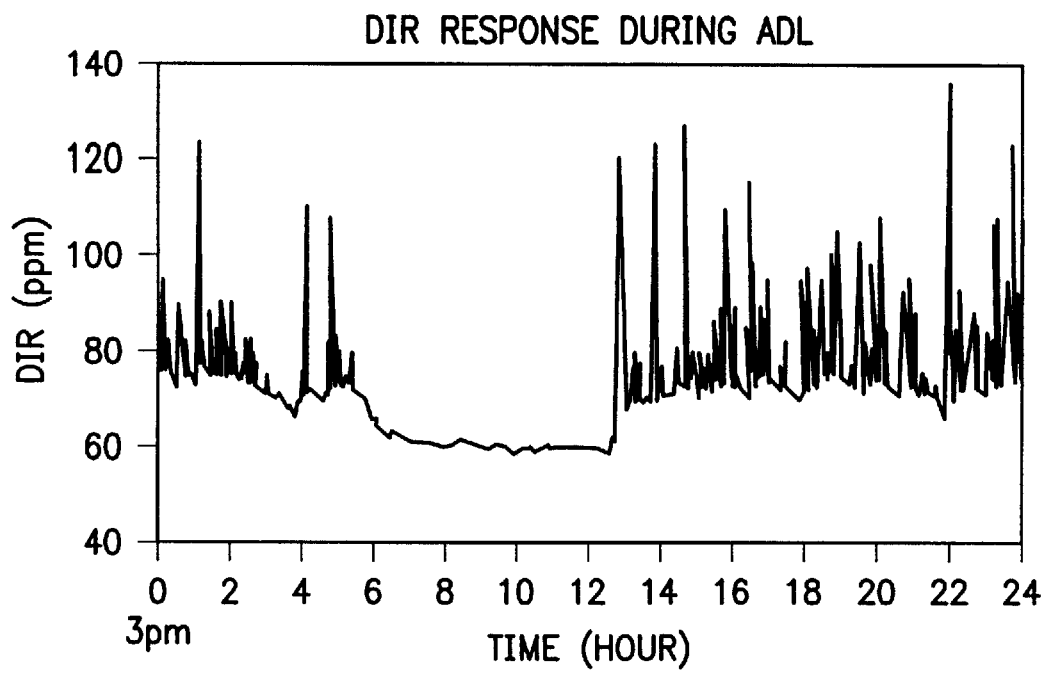

FIGS. 4A through 4D illustrate the correspondence between the intrinsic sinus rate of a patient wearing a Holter monitor and a calculated activity indicated rate, metabolic indicated rate, and dual indicated rate for 24 hours of a daily living period using the algorithm of FIG. 2. In these examples, the algorithm was tested using a 24-hour Holter monitor in which a normal healthy subject was equipped with a taped on accelerometer, and transthoracic impedance and ECG signals were also recorded during this time period. As is demonstrated by a comparison of FIG. 4D to the normal sinus rhythm of FIG. 4A, the DIR tracks the intrinsic sinus rhythm with a good degree of correspondence. In this embodiment, the DIR is adapted to follow the sleep mode of the AIR during the periods of approximately Hour 6 to Hour 13 where the activity indicated rate (AIR) dropped below the rest rate threshold as shown in FIG. 4B. Hence, comparison of these figures indicates that the dual indicated rate (DIR) determined by selecting a maximum between the activity indicated rate (AIR) and the metabolic indicated rate (MIR) results in a dual indicated rate (DIR) that has a relatively high degree of correspondence to a desired intrinsic sinus rate during average daily living.

Figure 5A:
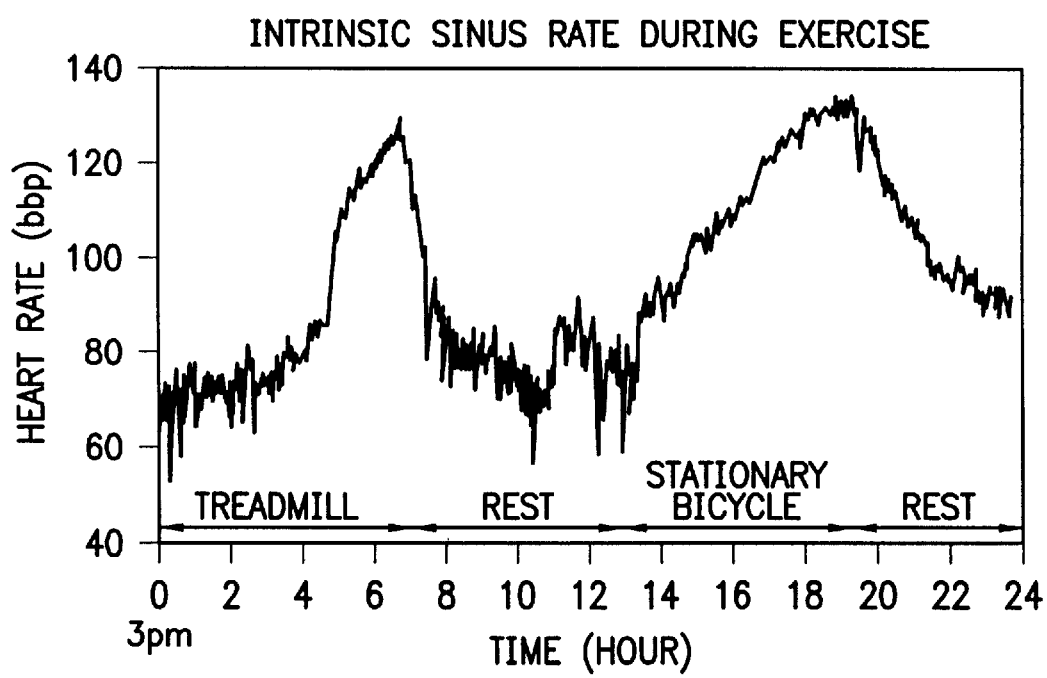
FIGS. 5A–5D are diagrams illustrating the intrinsic sinus rate, the activity indicated rate, the minute ventilation indicated rate and the dual indicated rate as determined according to the algorithm of FIG. 2 for a patient engaged in high level sustained exercise.
Figure 5B:
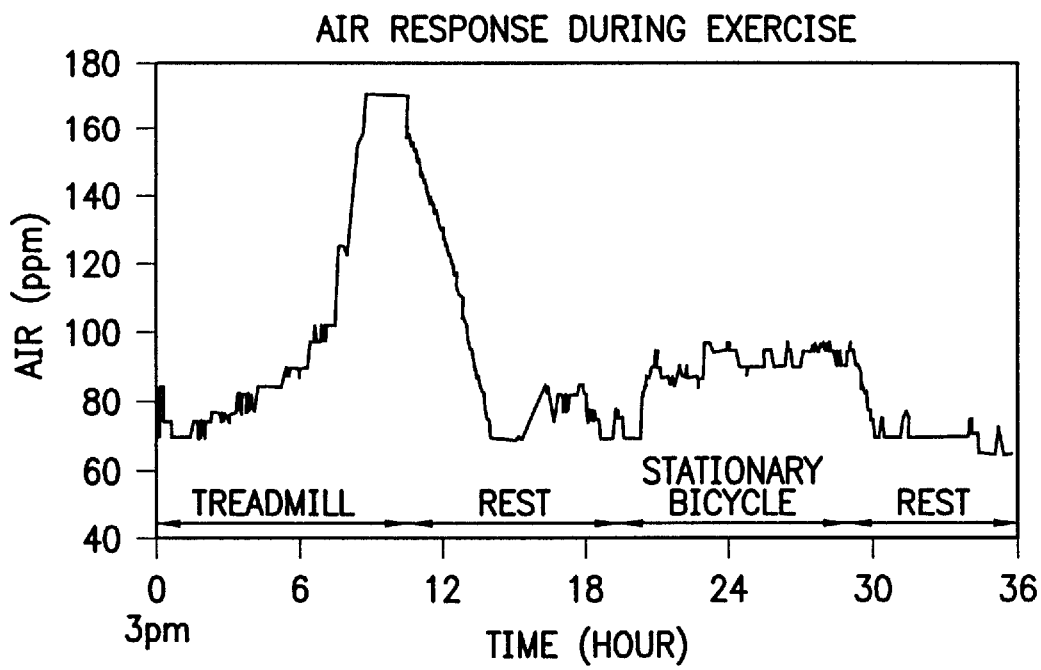
Figure 5C:
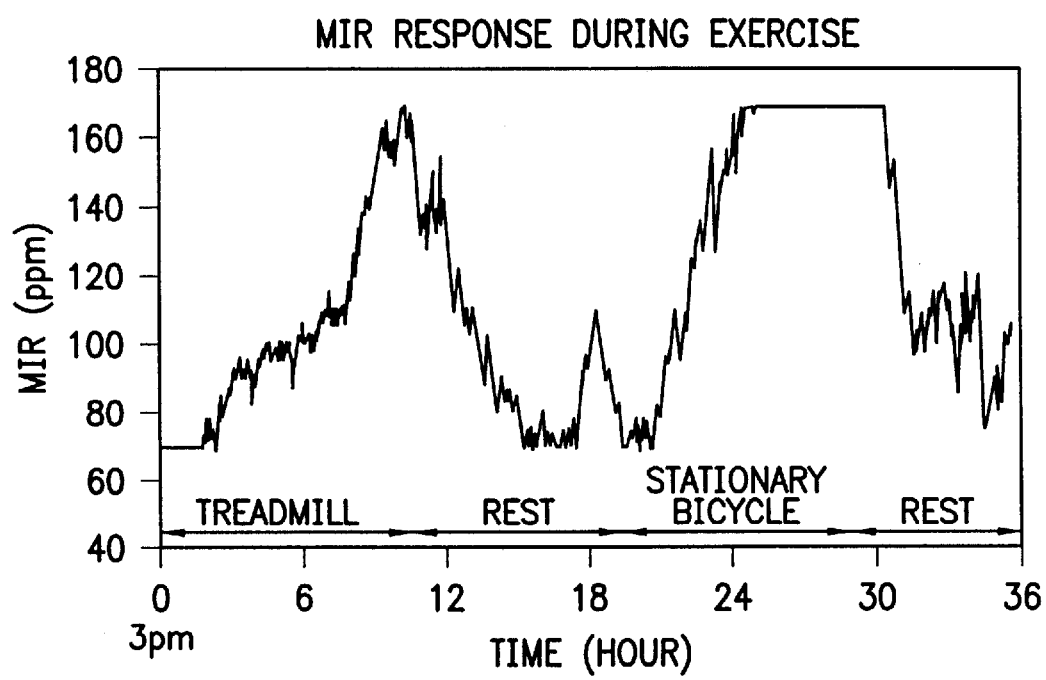
Figure 5D:
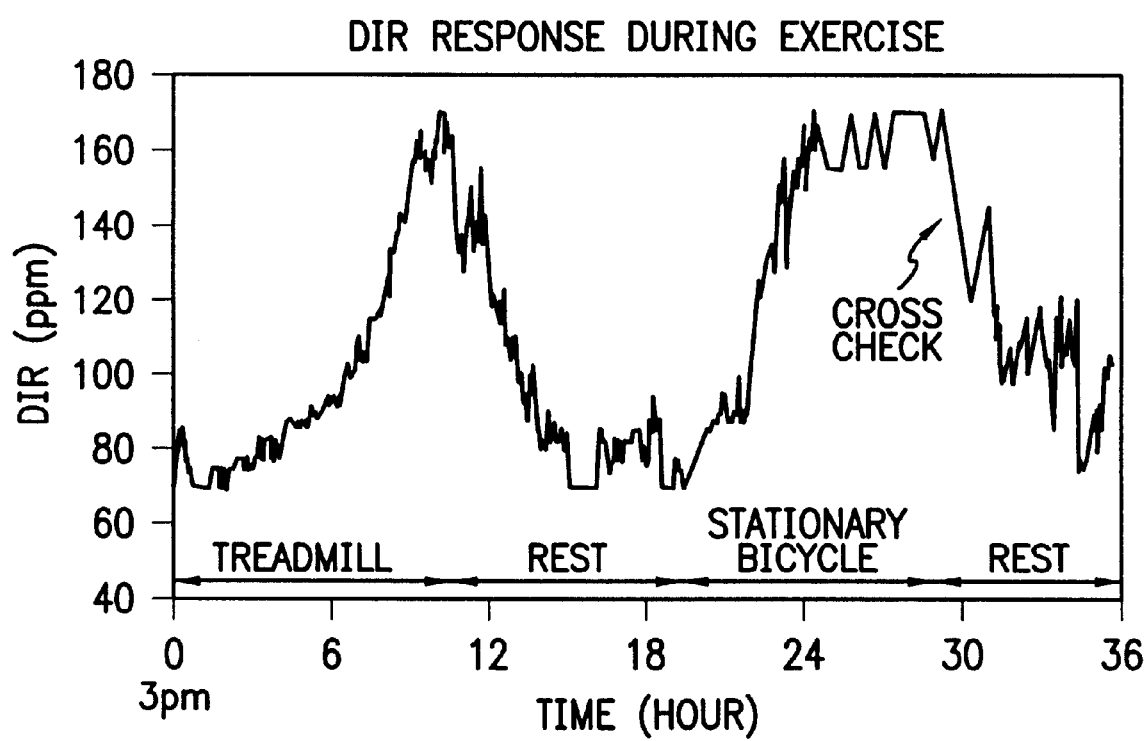

FIGS. 5A–5D illustrate the intrinsic sinus rate, the AIR response, the MIR response and the DIR response (calculated according to the algorithm of FIG. 2), respectively, during a high level of sustained exercise of a particular patient. These figures demonstrate that when one sensor fails to provide an indicated rate that corresponds to the desired intrinsic sinus rate as illustrated in FIG. 5A, the other sensor will provide a rate that corresponds to the intrinsic sinus rate of FIG. 5A. In fact, a comparison of the DIR response during the exercise illustrated in FIG. 5D to the intrinsic sinus rate during the exercise illustrates that the DIR waveform over the treadmill, rest, stationary bike, rest period has a high degree of correspondence with the intrinsic sinus rate during these time periods. Further, as illustrated by FIG. 5B, the AIR does not track the graded stationary bike exercise with the increased workload, however, the MIR does track the increased metabolic need and the DIR during this time period is using the MIR value. As is further illustrated in FIG. 5D, the cross-checking algorithm occurred during a period after about 30 minutes of exercise when the AIR indicated that the patient was approaching an at-rest situation, but the MIR indicated that the patient still had a high metabolic demand. This resulted in a gradual lowering of the DIR to intermediate values until the MIR signal provided by the metabolic sensor 132 was less than a maximum threshold amount.

From the foregoing, it will be appreciated that the algorithm for determining a dual or desired indicated rate that can be used by the processor 120 of the pacing system 100 provides a simple algorithm for determining a desired heart rate for the patient over a range of average daily living and specific instances of exercise. During each period of exercise, it is comparatively easy to ascertain the origins of the dual indicated rate from between either the activity indicated rate or the metabolic indicated rate for diagnostic purposes. Moreover, the DIR as determined by the algorithm used in the preferred embodiment, provides a high degree of correspondence with the normal sinus rates of the patient illustrated in FIGS. 4A–D and FIGS. 5A–D.

Numerous variations and modifications of the invention will become readily apparent to those skilled in the art. Accordingly, the invention may be embodied in other specific forms without departing from the spirit or essential characteristics of the present invention. The detailed embodiment is to be considered in all respects only as illustrative and not restrictive and the scope of the invention is, therefore, indicated by the appended claims rather than by the foregoing description. All changes which come within the meaning and range of the equivalency of the claims are to be embraced within their scope.

What is claimed is:

1. A pacing system comprising:
    activity rate sensor means for generating an activity indicated rate signal dependent upon the sensed activity of the patient;
    metabolic rate sensor means for generating a metabolic indicated rate signal dependent upon a metabolic demand of the patient in response to physical activity of the patient;
    dual indicated rate determining means for determining, based upon the activity indicated rate signal and the metabolic indicated rate signal, a dual indicated rate for pacing the patient, wherein the dual indicated rate determining means sets the dual indicated rate to correspond to the greater of the activity indicated rate signal or the metabolic indicated rate signal, the dual indicated rate determining means otherwise setting the dual indicated rate as corresponding to a rest rate when either the activity indicated rate signal or the metabolic indicated rate signal indicates that the patient is at rest; and
    pacing means for providing pacing signals to the heart of the patient in response to the determined dual indicated rate.

2. The system of claim 1, wherein the activity rate sensor means comprises an activity sensor that senses acceleration of the patient's body in response to activity of the patient and generates the activity indicated rate signal therefrom.

3. The system of claim 2, wherein the metabolic rate sensor means comprises a transthoracic impedance measurement circuit that periodically obtains a transthoracic impedance measurement which is then used to determine a minute ventilation parameter upon which the metabolic indicated rate signal is based.

4. The system of claim 1, wherein the dual indicated rate determining means sets the dual indicated rate as corresponding to a rest rate that is equal to the larger of the activity indicated rate signal or the metabolic indicated rate signal when both the activity indicated rate signal and the metabolic indicated rate signal are indicating that the patient is at rest.

5. The system of claim 4, wherein the dual indicated rate determining means sets the dual indicated rate as corresponding to a rest rate that is equal to one of the activity indicated rate signal or the metabolic indicated rate signal when one of the activity indicated rate signals or the metabolic indicated rate signal is indicating that the patient is at rest.

6. The system of claim 4, wherein the preselected maximum value of the activity indicated rate signal is set by a treating physician at implantation of the pacing system into the patient.

7. The system of claim 1, wherein the dual indicated rate determining means limits the magnitude of the activity indicated rate signal to a preselected maximum value when the activity indicated rate signal exceeds the preselected maximum value prior to the dual indicated rate determining means setting the dual indicated rate as corresponding to the greater of the activity indicated rate signal or the metabolic indicated rate signal, such that if the metabolic indicated rate signal exceeds the preselected maximum value of the activity indicated rate signal, the dual indicated rate determining means sets the dual indicated rate as corresponding to the metabolic indicated rate signal.

8. The system of claim 7, wherein the preselected maximum value of the activity indicated rate signal (CAIR) is determined according to the following formula:

$$CAIR = 0.7*(220-Age) - 10 \text{ pulses per minute}$$

wherein the Age is equal to the age of the patient.

9. The system of claim 1, wherein the dual indicated rate determining means determines whether the activity indicated rate signal is less than a preselected threshold value when the metabolic indicated rate signal exceeds a preselected threshold value and sets the dual indicated rate as being equal to an intermediate value selected to be between the metabolic indicated rate signal and the activity indicated rate signal.

10. The system of claim 9, wherein the dual indicated rate determining means continues to set the dual indicated rate at an intermediate value until the metabolic indicated rate signal decreases below the preselected threshold so that the pacing signals are provided to the heart at a progressively slower rate.

11. An implantable pacing system for providing pacing pulses to a patient, the system comprising:
    at least one lead adapted to be implanted adjacent the heart of the patient so as to be able to deliver pacing pulses to the heart of the patient;
    an activity sensor adapted to be implanted within the body of the patient, wherein the activity sensor periodically produces an activity signal corresponding to the sensed level of activity of the patient;
    a metabolic sensor adapted to be implanted within the body of the patient, wherein the metabolic sensor periodically produces a metabolic signal corresponding to the sensed metabolic demand of the patient;
    a control unit adapted to be implanted within the body of the patient, wherein the control unit receives the activity signal and periodically determines an activity indicated rate therefrom indicative of a pacing rate corresponding to the sensed level of activity of the patient, wherein the control unit also receives the metabolic signal and periodically determines a metabolic indicated rate therefrom indicative of a pacing rate corresponding to the sensed metabolic demand of the patient, wherein the metabolic indicated rate and the activity indicated rate are scaled so as to correspond to each other and wherein the control unit periodically determines a dual indicated rate by selecting the greater of the activity indicated rate and the metabolic indicated rate, wherein the activity indicated rate is generally more indicative of the patient's physiological need during periods of low exercise and initiation of exercise and is selected to have a higher magnitude than the metabolic indicated rate during these periods such that during periods of low exercise and initiation of exercise, the dual indicated rate generally corresponds to the activity indicated rate and induces the delivery of pacing pulses to the heart of the patient via the at least one lead so that the heart rate of the heart is maintained at a rate corresponding to the dual indicated rate.

12. The pacing system of claim 11, wherein the activity sensor is comprised of a sensor that senses the acceleration of the patient's body in response to activity of the patient.

13. The pacing system of claim 11, wherein the metabolic sensor comprises a transthoracic impedance measurement circuit that periodically measures the transthoracic impedance that is indicative of a minute ventilation parameter of the patient.

14. The pacing system of claim 11, wherein the activity indicated rate is generally more indicative of the patient's physiological need during periods of low exercise and initiation of exercise and is selected to have a higher magnitude than the metabolic indicated rate during these periods such that during periods of low exercise and initiation of exercise, the dual indicated rate generally corresponds to the activity indicated rate.

15. The pacing system of claim 11, wherein the metabolic indicated rate generally is more indicative of the patient's physiological need during periods of high exertion exercise and is selected to have a higher magnitude than the activity indicated rate during these periods such that during periods of high exertion exercise the dual indicated rate generally corresponds to the metabolic indicated rate.

16. The pacing system of claim 15, wherein the control unit limits the magnitude of the activity indicated rate to a preselected maximum value when the determined magnitude of the activity indicated rate would exceed the preselected maximum value, such that when the magnitude of the metabolic indicated rate exceeds the preselected maximum value for magnitude of the activity indicated rate, the control unit sets the dual indicated rate as corresponding to the metabolic indicated rate.

17. The pacing system of claim 16, wherein the control unit sets the magnitude of the dual indicated rate to the preselected maximum value for the activity indicated rate when the magnitude of the metabolic indicated rate is less than the magnitude of the preselected maximum value for the activity indicated rate and the determined magnitude of the activity indicated rate would exceed the preselected maximum value.

18. The system of claim 17, wherein the preselected maximum value of the magnitude of the activity indicated rate is set by a treating physician at implantation of the pacing system into the patient.

19. The system of claim 17, wherein the preselected maximum value of the magnitude of the activity indicated rate (CAIR) is determined according to the following formula:

$$CAIR = 0.7*(220 - Age) - 10 \text{ pulses per minute}$$

wherein the Age is equal to the age of the patient.

20. The system of claim 11, wherein the control unit evaluates the activity signal and the metabolic signal and determines whether either the metabolic signal or the activity signal indicates that the patient is at rest and, if the patient is determined to be at rest, the control unit then sets the dual indicated rate to correspond to a predetermined rest rate.

21. The system of claim 20, wherein the control unit sets the dual indicating rate as corresponding to a rest rate that is equal to the larger of the activity indicated rate or the metabolic indicated rate when both the activity indicated rate and the metabolic indicated rate are indicating that the patient is at rest.

22. The system of claim 21, wherein the control unit sets the dual indicated rate as corresponding to a rest rate that is equal to one of the activity indicated rates or the metabolic indicated rate when one of the activity indicated rates or the metabolic indicated rate is indicating that the patient is at rest.

23. The system of claim 11, wherein the control unit determines whether the magnitude of the activity indicated rate is less than a first preselected threshold value when the metabolic indicated rate exceeds a second preselected threshold value and sets the dual indicated rate as corresponding to an intermediate value selected to be between the magnitude of the metabolic indicated rate and the activity indicated rate.

24. The system of claim 23, wherein the control unit successively sets the dual indicated rate to correspond to an intermediate value between the magnitude of the activity indicated rate and the magnitude of the metabolic indicated rate until the magnitude of the metabolic indicated rate is less than the second preselected threshold value so that during periods following high exertion exercise the dual indicated rate is more gradually lowered.

25. A method of determining a pacing rate of a heart of a patient, the method comprising:
  sensing an activity parameter of the patient comprising sensing the acceleration of the patient's body to obtain an indication of the level of activity of the patient;
  sensing a metabolic parameter of the patient;
  determining an activity indicated rate based upon the sensed activity parameter of the patient;
  determining a metabolic indicated rate based upon the sensed metabolic parameter of the patient; and
  setting a dual indicated rate to be the greater of the activity indicated rate or the metabolic indicated rate, wherein the dual indicated rate corresponds to the rate at which the heart rate of the heart of the patient is to be maintained to meet the metabolic needs of the patient based upon the sensed activity and metabolic parameters.

26. The method of claim 25, further comprising scaling the activity indicated rate and the metabolic indicated rate so that the activity indicated rate and the metabolic indicated rate correspond to each other.

27. The method of claim 25, wherein sensing a metabolic parameter of the patient comprises sensing the transthoracic impedance of the patient to obtain a minute ventilation parameter indicative of the metabolic demand of the patient.

28. The method of claim 27, wherein setting a dual indicated rate to be the greater of the activity indicated rate or the metabolic indicated rate comprises setting the dual indicated rate to be the metabolic indicated rate when the metabolic indicated rate exceeds the preselected maximum of the activity indicated rate.

29. The method of claim 28, wherein setting the dual indicated rate to be the greater of the activity indicated rate or the metabolic indicated rate comprises setting the dual indicated rate to be the preselected maximum of the activity indicated rate when the metabolic indicated rate is less than the preselected maximum and the activity indicated rate would exceed the preselected maximum.

30. A pacing system comprising:
    a plurality of independently functioning rate sensors, said plurality comprising activity rate sensor means and metabolic sensor means;
    the activity rate sensor means, functioning independently from the metabolic sensor means, for generating an activity indicated rate signal dependent upon the sensed activity of the patient;
    the metabolic rate sensor means, functioning independently from the activity rate sensor means, for generating a metabolic indicated rate signal dependent upon a metabolic demand of the patient in response to physical activity of the patient;
    dual indicated rate determining means for determining, based upon the activity indicated rate signal and the metabolic indicated rate signal, a dual indicated rate for pacing the patient, wherein the dual indicated rate determining means sets the dual indicated rate to correspond to the greater of the activity indicated rate signal or the metabolic indicated rate signal; and
    pacing means for providing pacing signals to the heart of the patient in response to the dual indicated rate.

31. The system of claim 30, further comprising means for setting the dual indicated rate as corresponding to a rest rate when either the activity indicated rate signal or the metabolic indicated rate signal indicates that the patient is at rest.

32. The system of claim 31, further comprising means for setting the dual indicated rate as corresponding to a rest rate that is equal to the larger of the activity indicated rate signal or the metabolic indicated rate signal when both the activity indicated rate signal and the metabolic indicated rate signal are indicating that the patient is at rest.

33. The system of claim 32, further comprising means for setting the dual indicated rate as corresponding to a rest rate that is equal to one of the activity indicated rate signal or the metabolic indicated rate signal when one of the activity indicated rate signals or the metabolic indicated rate signal is indicating that the patient is at rest.

34. The system of claim 30, wherein the activity rate sensor means comprises an activity sensor that senses acceleration of the patient's body in response to activity of the patient and generates the activity indicated rate signal therefrom.

35. The system of claim 30, wherein the metabolic rate sensor means comprises a transthoracic impedance measurement circuit that periodically obtains a transthoracic impedance measurement which is then used to determine a minute ventilation parameter upon which the metabolic indicated rate signal is based.

36. The system of claim 30, further comprising means for determining whether the activity indicated rate signal is less than a preselected threshold value when the metabolic indicated rate signal exceeds a preselected threshold value and sets the dual indicated rate as being equal to an intermediate value selected to be between the metabolic indicated rate signal and the activity indicated rate signal.

37. The system of claim 36, including means for continuing to set the dual indicated rate at an intermediate value until the metabolic indicated rate signal decreases below the preselected threshold so that the pacing signals are provided to the heart at a progressively slower rate.

38. A method of determining a pacing rate of a heart of a patient, the method comprising the steps of:
    sensing an activity parameter of the patient;
    sensing a metabolic parameter of the patient;
    determining an activity indicated rate based upon the sensed activity parameter of the patient;
    determining whether the activity indicated rate exceeds a preselected maximum rate;
    setting the activity indicated rate to the preselected maximum rate when the activity indicated rate exceeds the preselected maximum rate;
    determining a metabolic indicated rate based upon the sensed metabolic parameter of the patient; and
    setting a dual indicated rate to be the greater of the metabolic indicated rate and the activity indicated rate, wherein the dual indicated rate corresponds to the rate at which the heart rate of the heart of the patient is to be maintained to meet the metabolic needs of the patient based upon the sensed activity and metabolic parameters.

39. A method of determining a pacing rate of a heart of a patient, the method comprising the steps of:
    sensing an activity parameter of the patient
    sensing a metabolic parameter of the patient;
    determining an activity indicated rate based upon the sensed activity parameter of the patient;
    determining a metabolic indicated rate based upon the sensed metabolic parameter of the patient; and determining whether the activity indicated rate is less than a preselected threshold value when the metabolic indicated rate exceeds a preselected threshold value and wherein setting a dual indicated rate, when the activity indicated rate is less than a preselected threshold value and when the metabolic indicated rate exceeds a preselected value, comprises setting the dual indicated rate to an intermediate value which is between the metabolic indicated rate and the activity indicated rate to thereby slow the heart rate more slowly, wherein the dual indicated rate corresponds to the rate at which the heart rate of the heart of the patient is to be maintained to meet the metabolic needs of the patient based upon the sensed activity and metabolic parameters.

40. A method of determining a pacing rate of a heart of a patient, the method comprising the steps of:
    sensing an activity parameter of the patient;
    sensing a metabolic parameter of the patient;
    determining an activity indicated rate based upon the sensed activity parameter of the patient;
    determining a metabolic indicated rate based upon the sensed metabolic parameter of the patient;
    determining whether the activity indicated rate or the metabolic indicated rate indicates that the patient is at rest; and
    setting a dual indicated rate to a rest rate when it is determined that the patient is at rest, otherwise setting the dual indicated rate to be the greater of the activity indicated rate or the metabolic indicated rate, wherein the dual indicated rate corresponds to the rate at which the heart rate of the heart of the patient is to be maintained to meet the metabolic needs of the patient based upon the sensed activity and metabolic parameters.

* * * * *